(12) United States Patent
Taylor et al.

(10) Patent No.: US 10,354,050 B2
(45) Date of Patent: *Jul. 16, 2019

(54) IMAGE PROCESSING METHOD FOR DETERMINING PATIENT-SPECIFIC CARDIOVASCULAR INFORMATION

(71) Applicant: BOARD OF TRUSTEES OF THE LELAND STANFORD JUNIOR UNIVERSITY, Palo Alto, CA (US)

(72) Inventors: Charles A. Taylor, Menlo Park, CA (US); Hyun Jin Kim, San Mateo, CA (US); Jessica S. Coogan, Palo Alto, CA (US)

(73) Assignee: THE BOARD OF TRUSTEES OF LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/196,836

(22) Filed: Jun. 29, 2016

(65) Prior Publication Data
US 2016/0378947 A1  Dec. 29, 2016

Related U.S. Application Data

(63) Continuation of application No. 12/661,491, filed on Mar. 17, 2010, now Pat. No. 9,405,886.

(60) Provisional application No. 61/210,401, filed on Mar. 17, 2009.

(51) Int. Cl.
| G06F 19/00 | (2018.01) |
| G06T 19/00 | (2011.01) |
| G16H 10/60 | (2018.01) |
| G16H 30/00 | (2018.01) |
| G16H 30/20 | (2018.01) |
| G16H 30/40 | (2018.01) |
| G16H 50/50 | (2018.01) |

(52) U.S. Cl.
CPC .......... *G06F 19/321* (2013.01); *G16H 10/60* (2018.01); *G16H 30/00* (2018.01); *G16H 30/20* (2018.01); *G16H 30/40* (2018.01); *G16H 50/50* (2018.01); *G06T 19/00* (2013.01)

(58) Field of Classification Search
None
See application file for complete search history.

(56) References Cited

U.S. PATENT DOCUMENTS

| 4,821,735 A | 4/1989 | Goor et al. |
| 4,945,478 A | 7/1990 | Merickel et al. |
| 5,119,816 A | 6/1992 | Gevins |
| 5,151,856 A | 9/1992 | Halmann et al. |
| 5,205,289 A | 4/1993 | Hardy et al. |
| 5,235,510 A | 8/1993 | Yamada et al. |
| 5,582,173 A | 12/1996 | Li |
| 5,682,886 A | 11/1997 | Delp et al. |
| 5,687,208 A | 11/1997 | Bae et al. |
| 5,687,737 A | 11/1997 | Branham et al. |
| 5,729,670 A | 3/1998 | Strumolo et al. |
| 5,740,802 A | 4/1998 | Nafis et al. |
| 5,782,762 A | 7/1998 | Vining |
| 5,825,908 A | 10/1998 | Pieper et al. |
| 5,871,018 A | 2/1999 | Delp et al. |
| 5,920,319 A | 7/1999 | Vining et al. |
| 5,947,899 A | 9/1999 | Winslow et al. |
| 6,026,173 A | 2/2000 | Svenson et al. |
| 6,047,080 A | 4/2000 | Chen et al. |
| 6,083,162 A | 7/2000 | Vining |
| 6,117,087 A | 9/2000 | Kamm |
| 6,169,917 B1 | 1/2001 | Masotti et al. |
| 6,176,838 B1 | 1/2001 | Sase |
| 6,236,878 B1 | 5/2001 | Taylor |
| 6,272,366 B1 | 8/2001 | Vining |

(Continued)

FOREIGN PATENT DOCUMENTS

| CN | 1600268 A | 3/2005 |
| CN | 201015590 Y | 2/2008 |

(Continued)

OTHER PUBLICATIONS

Migliavacca et al. (Journal of Biomechanics (2006) vol. 39:1010-1020).*
Formaggia et al. (Computational Methods Appl. Mech. Engrg. (2001) vol. 191, pp. 561-582).*
Fernandez et al. (Computational Fluid and Solid Mechanics (2003) in Second MIT Conference on Computational Fluid and Solid Mechanics: 1337-1341.*
Computational Analysis of Flow in a Curved Tube Model of the Coronary Arteries: Effects of Time-varying Curvature. Santamarina et al., Annals of Biomedical Engineering, 26:944-954, 1998.
Computational simulation of intracoronary flow based on real coronary geometry, Boutsianis et al., European Journal of Cardio-thoracic Surgery 26:248-256, 2004.

(Continued)

*Primary Examiner* — Lori A. Clow
(74) *Attorney, Agent, or Firm* — Bookoff McAndrews, PLLC

(57) ABSTRACT

A noninvasive patient-specific method is provided to aid in the analysis, diagnosis, prediction or treatment of hemodynamics of the cardiovascular system of a patient. Coronary blood flow and pressure can be predicted using a 3-D patient image-based model that is implicitly coupled with a model of at least a portion of the remaining cardiovascular system. The 3-D patient image-based model includes at least a portion of the thoracic aorta and epicardial coronaries of the patient. The shape of one or more velocity profiles at the interface of the models is enforced to control complex flow features of recirculating or retrograde flow thereby minimizing model instabilities and resulting in patient-specific predictions of coronary flow rate and pressure. The invention allows for patient-specific predictions of the effect of different or varying physiological states and hemodynamic benefits of coronary medical interventions, percutaneous coronary interventions and surgical therapies.

14 Claims, 3 Drawing Sheets

(56) References Cited

U.S. PATENT DOCUMENTS

| | | |
|---|---|---|
| 6,278,460 B1 | 8/2001 | Myers et al. |
| 6,352,509 B1 | 3/2002 | Kawagishi et al. |
| 6,366,800 B1 | 4/2002 | Vining et al. |
| 6,379,041 B1 | 4/2002 | Schuetz et al. |
| 6,381,562 B2 | 4/2002 | Keane |
| 6,408,201 B1 | 6/2002 | Foo et al. |
| 6,442,235 B2 | 8/2002 | Koppe et al. |
| 6,466,205 B2 | 10/2002 | Simpson et al. |
| 6,471,656 B1 | 10/2002 | Shalman et al. |
| 6,478,735 B1 | 11/2002 | Pope et al. |
| 6,487,432 B2 | 11/2002 | Slack |
| 6,500,117 B1 | 12/2002 | Hancock, Jr. |
| 6,501,848 B1 | 12/2002 | Carroll et al. |
| 6,503,202 B1 | 1/2003 | Hossack et al. |
| 6,507,753 B1 | 1/2003 | Xue et al. |
| 6,606,091 B2 | 8/2003 | Liang et al. |
| 6,628,743 B1 | 9/2003 | Drummond et al. |
| 6,650,724 B2 | 11/2003 | Strobel |
| 6,666,820 B1 | 12/2003 | Poole |
| 6,694,163 B1 | 2/2004 | Vining |
| 6,711,433 B1 | 3/2004 | Geiger et al. |
| 6,718,004 B2 | 4/2004 | Cesmeli |
| 6,720,966 B2 | 4/2004 | Barth et al. |
| 6,793,496 B2 | 9/2004 | Edic et al. |
| 6,801,643 B2 | 10/2004 | Pieper |
| 6,887,207 B2 | 5/2005 | Hettrick |
| 6,898,453 B2 | 5/2005 | Lee |
| 6,909,913 B2 | 6/2005 | Vining |
| 6,932,842 B1 | 8/2005 | Litschko et al. |
| 6,950,689 B1 | 9/2005 | Willis et al. |
| 6,996,262 B2 | 2/2006 | Li |
| 7,006,955 B2 | 2/2006 | Daft et al. |
| 7,121,832 B2 | 10/2006 | Hsieh et al. |
| 7,149,333 B2 | 12/2006 | Pieper et al. |
| 7,149,564 B2 | 12/2006 | Vining et al. |
| 7,182,602 B2 | 2/2007 | Lakin et al. |
| 7,191,110 B1 | 3/2007 | Charbel |
| 7,229,412 B2 | 6/2007 | Jacob et al. |
| 7,286,866 B2 | 10/2007 | Okerlund et al. |
| 7,302,286 B2 | 11/2007 | Camus et al. |
| 7,321,677 B2 | 1/2008 | Evron et al. |
| 7,327,862 B2 | 2/2008 | Murphy et al. |
| 7,333,643 B2 | 2/2008 | Murphy et al. |
| 7,333,648 B2 | 2/2008 | Edic et al. |
| 7,343,196 B2 | 3/2008 | Okerlund et al. |
| 7,356,367 B2 | 4/2008 | Liang et al. |
| 7,369,691 B2 | 5/2008 | Kondo et al. |
| 7,371,067 B2 | 5/2008 | Anderson et al. |
| 7,462,153 B2 | 12/2008 | Bostian et al. |
| 7,474,776 B2 | 1/2009 | Kaufman et al. |
| 7,505,551 B2 | 3/2009 | Grass et al. |
| 7,526,112 B2 | 4/2009 | Murphy et al. |
| 7,536,042 B2 | 5/2009 | Murphy et al. |
| 7,539,529 B2 | 5/2009 | Schmitt et al. |
| 7,542,595 B2 | 6/2009 | Moreau-Gobard |
| 7,574,026 B2 | 8/2009 | Rasche et al. |
| 7,646,900 B2 | 1/2010 | Movassaghi et al. |
| 7,646,901 B2 | 1/2010 | Murphy et al. |
| 7,650,179 B2 | 1/2010 | Redel et al. |
| 7,657,299 B2 | 2/2010 | Huizenga et al. |
| 7,693,563 B2 | 4/2010 | Suresh et al. |
| 7,725,164 B2 | 5/2010 | Suurmond et al. |
| 7,725,165 B2 | 5/2010 | Chen et al. |
| 7,738,626 B2 | 6/2010 | Weese et al. |
| 7,739,090 B2 | 6/2010 | Charbel et al. |
| 7,742,629 B2 | 6/2010 | Zarkh et al. |
| 7,747,055 B1 | 6/2010 | Vining et al. |
| 7,751,984 B2 | 7/2010 | Tang |
| 7,773,719 B2 | 8/2010 | Galant et al. |
| 7,773,785 B2 | 8/2010 | Murphy et al. |
| 7,792,565 B2 | 9/2010 | Vining |
| 7,792,593 B2 | 9/2010 | Rahn et al. |
| 7,805,177 B2 | 9/2010 | Chen et al. |
| 7,813,785 B2 | 10/2010 | Okerlund et al. |
| 7,853,310 B2 | 12/2010 | Vining et al. |
| 8,157,742 B2 | 4/2012 | Taylor |
| 8,315,812 B2 | 11/2012 | Taylor |
| 8,321,150 B2 | 11/2012 | Taylor |
| 8,366,629 B2 | 2/2013 | Bardy |
| 8,447,552 B2 | 5/2013 | Abraham-Fuchs et al. |
| 8,731,968 B1 | 5/2014 | Iliff |
| 8,831,320 B2 | 9/2014 | Bernhardt et al. |
| 9,405,996 B2 | 8/2016 | Ionasec et al. |
| 2002/0002447 A1 | 1/2002 | Keane |
| 2002/0035458 A1 | 3/2002 | Kim et al. |
| 2002/0052553 A1 | 5/2002 | Shalman et al. |
| 2002/0118869 A1 | 8/2002 | Knoplioch et al. |
| 2002/0120431 A1 | 8/2002 | Keane |
| 2002/0168618 A1 | 11/2002 | Anderson et al. |
| 2003/0023266 A1 | 1/2003 | Borillo et al. |
| 2003/0083582 A1 | 5/2003 | Hirsh |
| 2003/0123606 A1 | 7/2003 | Mollus et al. |
| 2003/0204160 A1 | 10/2003 | Kamm et al. |
| 2004/0034309 A1 | 2/2004 | Pullan et al. |
| 2004/0044282 A1 | 3/2004 | Mixon et al. |
| 2004/0049115 A1 | 3/2004 | Murphy et al. |
| 2004/0064298 A1 | 4/2004 | Levine |
| 2004/0153128 A1 | 8/2004 | Suresh et al. |
| 2005/0010105 A1 | 1/2005 | Sra |
| 2005/0018885 A1 | 1/2005 | Chen et al. |
| 2005/0043609 A1 | 2/2005 | Murphy et al. |
| 2005/0059876 A1 | 3/2005 | Krishnan et al. |
| 2005/0064416 A1 | 3/2005 | Fishman et al. |
| 2005/0131663 A1 | 6/2005 | Bangs et al. |
| 2005/0249717 A1 | 11/2005 | Burgard et al. |
| 2005/0272992 A1 | 12/2005 | O'Donnell et al. |
| 2006/0069318 A1 | 3/2006 | Keaveny et al. |
| 2006/0142984 A1 | 6/2006 | Weese et al. |
| 2006/0149522 A1 | 7/2006 | Tang |
| 2006/0166176 A1 | 7/2006 | Lakin et al. |
| 2006/0171585 A1 | 8/2006 | Rinck et al. |
| 2006/0235669 A1 | 10/2006 | Charbel et al. |
| 2006/0239524 A1 | 10/2006 | Desh et al. |
| 2006/0239528 A1 | 10/2006 | Camus et al. |
| 2006/0241445 A1 | 10/2006 | Altmann et al. |
| 2006/0241461 A1 | 10/2006 | White et al. |
| 2006/0253024 A1 | 11/2006 | Altmann et al. |
| 2006/0278245 A1 | 12/2006 | Gan |
| 2007/0014452 A1 | 1/2007 | Suresh et al. |
| 2007/0015996 A1 | 1/2007 | Camus et al. |
| 2007/0078325 A1 | 4/2007 | Fuimaono et al. |
| 2007/0078352 A1 | 4/2007 | Pijls et al. |
| 2007/0135707 A1 | 6/2007 | Redel et al. |
| 2007/0163353 A1 | 7/2007 | Lec et al. |
| 2007/0219448 A1 | 9/2007 | Seip et al. |
| 2007/0231779 A1 | 10/2007 | Santhanam et al. |
| 2007/0232883 A1 | 10/2007 | Ilegbusi |
| 2007/0238999 A1 | 10/2007 | Specht |
| 2007/0276214 A1 | 11/2007 | Dachille et al. |
| 2007/0293936 A1 | 12/2007 | Dobak, III |
| 2008/0004508 A1 | 1/2008 | Sun et al. |
| 2008/0020362 A1 | 1/2008 | Cotin et al. |
| 2008/0040087 A1 | 2/2008 | Watrous |
| 2008/0044069 A1 | 2/2008 | Dugal |
| 2008/0051660 A1 | 2/2008 | Kakadaris et al. |
| 2008/0058642 A1 | 3/2008 | Gould |
| 2008/0069419 A1 | 3/2008 | Farag et al. |
| 2008/0097210 A1 | 4/2008 | Salgo et al. |
| 2008/0118121 A1 | 5/2008 | Skinner et al. |
| 2008/0118122 A1 | 5/2008 | Sirohey et al. |
| 2008/0133040 A1 | 6/2008 | Boyden et al. |
| 2008/0177172 A1 | 7/2008 | John et al. |
| 2008/0205722 A1 | 8/2008 | Schaefer et al. |
| 2008/0208068 A1 | 8/2008 | Robertson et al. |
| 2008/0212857 A1 | 9/2008 | Pfister et al. |
| 2008/0221442 A1 | 9/2008 | Tolkowsky et al. |
| 2008/0228086 A1 | 9/2008 | Ilegbusi et al. |
| 2008/0262346 A1 | 10/2008 | Assis et al. |
| 2008/0262814 A1 | 10/2008 | Zheng et al. |
| 2008/0269611 A1 | 10/2008 | Pedrizzetti et al. |
| 2008/0270095 A1 | 10/2008 | Lombaert et al. |
| 2008/0275336 A1 | 11/2008 | Deschamps et al. |
| 2008/0278492 A1 | 11/2008 | Ruijters et al. |
| 2008/0287812 A1 | 11/2008 | Parlikar et al. |

(56) References Cited

U.S. PATENT DOCUMENTS

| | | |
|---|---|---|
| 2008/0294038 A1 | 11/2008 | Weese et al. |
| 2008/0317310 A1 | 12/2008 | Suresh et al. |
| 2008/0319308 A1 | 12/2008 | Tang |
| 2009/0005672 A1 | 1/2009 | Sugiura |
| 2009/0008830 A1 | 1/2009 | Okazaki et al. |
| 2009/0012382 A1 | 1/2009 | Dutta et al. |
| 2009/0016483 A1 | 1/2009 | Kawasaki et al. |
| 2009/0028289 A1 | 1/2009 | Tsuyuki et al. |
| 2009/0054774 A1 | 2/2009 | Njemanze |
| 2009/0074267 A1 | 3/2009 | Pedrizzetti et al. |
| 2009/0077681 A1 | 3/2009 | Fishman et al. |
| 2009/0088830 A1 | 4/2009 | Mohamed et al. |
| 2009/0097731 A1 | 4/2009 | Sanada et al. |
| 2009/0116715 A1 | 5/2009 | Bredno et al. |
| 2009/0156933 A1 | 6/2009 | Gerard et al. |
| 2009/0161938 A1 | 6/2009 | Shekhar et al. |
| 2009/0177454 A1 | 7/2009 | Bronstein et al. |
| 2009/0221907 A1 | 9/2009 | Bar-Tal |
| 2009/0244061 A1 | 10/2009 | De Putter et al. |
| 2009/0281423 A1 | 11/2009 | Sirohey et al. |
| 2009/0281434 A1 | 11/2009 | Messerges et al. |
| 2009/0287135 A1 | 11/2009 | Michishita et al. |
| 2009/0292206 A1 | 11/2009 | Sato |
| 2009/0292349 A1 | 11/2009 | Golesworthy |
| 2009/0292557 A1 | 11/2009 | Sirohey et al. |
| 2009/0310840 A1 | 12/2009 | Mohamed et al. |
| 2009/0322749 A1 | 12/2009 | Kassab et al. |
| 2009/0324052 A1 | 12/2009 | Nowinski et al. |
| 2010/0002925 A1 | 1/2010 | Kiraly et al. |
| 2010/0017171 A1 | 1/2010 | Spilker et al. |
| 2010/0041981 A1 | 2/2010 | Kassab |
| 2010/0053209 A1 | 3/2010 | Rauch et al. |
| 2010/0067760 A1 | 3/2010 | Zhang et al. |
| 2010/0070249 A1 | 3/2010 | Ionasec et al. |
| 2010/0081917 A1 | 4/2010 | Zhang et al. |
| 2010/0086099 A1 | 4/2010 | Kuzmanovic |
| 2010/0121178 A1 | 5/2010 | Krishnan et al. |
| 2010/0125197 A1 | 5/2010 | Fishel |
| 2010/0130878 A1 | 5/2010 | Lasso et al. |
| 2010/0152570 A1 | 6/2010 | Navab |
| 2010/0156898 A1 | 6/2010 | Voros et al. |
| 2010/0172554 A1 | 7/2010 | Kassab et al. |
| 2010/0183206 A1 | 7/2010 | Carlsen et al. |
| 2010/0189337 A1 | 7/2010 | Jandt et al. |
| 2010/0241404 A1 | 9/2010 | Taylor et al. |
| 2010/0265251 A1 | 10/2010 | Vining et al. |
| 2010/0266176 A1 | 10/2010 | Masumoto et al. |
| 2010/0272315 A1 | 10/2010 | Tsin et al. |
| 2010/0278405 A1 | 11/2010 | Kakadiaris et al. |
| 2010/0280352 A1 | 11/2010 | Ionasec et al. |
| 2010/0298719 A1 | 11/2010 | Kock et al. |
| 2010/0299077 A1 | 11/2010 | Kassab et al. |
| 2010/0328305 A1 | 12/2010 | Vining |
| 2011/0060576 A1 | 3/2011 | Sharma et al. |
| 2011/0071404 A1 | 3/2011 | Schmitt et al. |
| 2011/0085977 A1 | 4/2011 | Rosenmeier |
| 2011/0131167 A1 | 6/2011 | Achterberg |
| 2011/0152599 A1 | 6/2011 | Bokeriya et al. |
| 2011/0178383 A1 | 7/2011 | Kassab |
| 2011/0178417 A1 | 7/2011 | Kassab |
| 2011/0275934 A1 | 11/2011 | Kassab |
| 2011/0275936 A1 | 11/2011 | Cho et al. |
| 2011/0282586 A1 | 11/2011 | Kassab et al. |
| 2012/0022843 A1 | 1/2012 | Ionasec et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0121151 A1 | 5/2012 | Bernhardt et al. |
| 2012/0122777 A1 | 5/2012 | Daimon et al. |
| 2012/0150516 A1 | 6/2012 | Taylor et al. |
| 2012/0243761 A1 | 9/2012 | Senzig et al. |
| 2013/0060133 A1 | 3/2013 | Kassab et al. |
| 2013/0090555 A1 | 4/2013 | Kassab |
| 2013/0132054 A1 | 5/2013 | Sharma et al. |
| 2013/0197884 A1 | 8/2013 | Mansi et al. |
| 2013/0226003 A1 | 8/2013 | Edic et al. |
| 2013/0246034 A1 | 9/2013 | Sharma et al. |
| 2013/0324842 A1 | 12/2013 | Mittal et al. |
| 2014/0029835 A1 | 1/2014 | Kim et al. |
| 2014/0073976 A1 | 3/2014 | Fonte et al. |
| 2014/0148693 A1 | 5/2014 | Taylor |
| 2014/0200867 A1 | 7/2014 | Lavi et al. |
| 2014/0243663 A1 | 8/2014 | Taylor |
| 2014/0249399 A1 | 9/2014 | Sharma et al. |
| 2015/0065864 A1 | 3/2015 | Sharma et al. |
| 2015/0112191 A1 | 4/2015 | Gilboa et al. |
| 2015/0265162 A1 | 9/2015 | Lavi et al. |
| 2015/0297161 A1 | 10/2015 | Grass et al. |
| 2015/0342551 A1 | 12/2015 | Lavi et al. |
| 2015/0356734 A1 | 12/2015 | Ooga et al. |
| 2016/0022371 A1 | 1/2016 | Sauer et al. |

FOREIGN PATENT DOCUMENTS

| | | |
|---|---|---|
| CN | 101172042 A | 5/2008 |
| EP | 0559919 A1 | 9/1993 |
| EP | 1125548 A1 | 8/2001 |
| EP | 1182819 A2 | 2/2002 |
| EP | 1225541 A2 | 7/2002 |
| EP | 1482470 A2 | 12/2004 |
| EP | 1492071 A1 | 12/2004 |
| EP | 0961993 B1 | 2/2005 |
| EP | 1717758 A2 | 11/2006 |
| EP | 1717759 A1 | 11/2006 |
| EP | 1961384 A1 | 8/2008 |
| EP | 1967140 A1 | 9/2008 |
| EP | 2028606 A1 | 2/2009 |
| EP | 2028608 A2 | 2/2009 |
| EP | 2138091 A1 | 12/2009 |
| EP | 2278597 A1 | 1/2011 |
| EP | 2302594 A2 | 3/2011 |
| EP | 2302595 A2 | 3/2011 |
| EP | 2302596 A1 | 3/2011 |
| JP | 2000515789 A | 11/2000 |
| JP | 2002501774 A | 1/2002 |
| JP | 2002513601 A | 5/2002 |
| JP | 2003508152 A | 3/2003 |
| JP | 2003525067 A | 8/2003 |
| JP | 2004528858 A | 9/2004 |
| JP | 2006230482 A | 9/2006 |
| JP | 2007135894 A | 6/2007 |
| JP | 2007517633 A | 7/2007 |
| JP | 2008009841 A | 1/2008 |
| JP | 2008126077 A | 6/2008 |
| JP | 2009515584 A | 4/2009 |
| JP | 2009523818 A | 6/2009 |
| JP | 2009195586 A | 9/2009 |
| JP | 2009540767 A | 11/2009 |
| JP | 2010115317 A | 5/2010 |
| JP | 2011040055 A | 2/2011 |
| JP | 2012501218 A | 1/2012 |
| JP | 2013505782 A | 2/2013 |
| KR | 20070026135 A | 3/2007 |
| KR | 20070120957 A | 12/2007 |
| KR | 20090093877 A | 9/2009 |
| KR | 20090098839 A | 9/2009 |
| WO | WO-9408315 A1 | 4/1994 |
| WO | WO-9526682 A1 | 10/1995 |
| WO | WO-9638815 A1 | 12/1996 |
| WO | WO-9641567 A2 | 12/1996 |
| WO | WO-9717894 A1 | 5/1997 |
| WO | WO-9749065 A1 | 12/1997 |
| WO | WO-9804182 A2 | 2/1998 |
| WO | WO-9811524 A1 | 3/1998 |

(56) References Cited

FOREIGN PATENT DOCUMENTS

| | | |
|---|---|---|
| WO | WO-9832371 A1 | 7/1998 |
| WO | WO-9843201 A1 | 10/1998 |
| WO | WO-9938433 A1 | 8/1999 |
| WO | WO-9942977 A1 | 8/1999 |
| WO | WO-9956612 A1 | 11/1999 |
| WO | WO-9963887 A1 | 12/1999 |
| WO | WO-0007501 A1 | 2/2000 |
| WO | WO-0032106 A1 | 6/2000 |
| WO | WO-0053081 A1 | 9/2000 |
| WO | WO-0055812 A1 | 9/2000 |
| WO | WO-0055814 A2 | 9/2000 |
| WO | WO-0068749 A1 | 11/2000 |
| WO | WO-0072272 A1 | 11/2000 |
| WO | WO-0117456 A1 | 3/2001 |
| WO | WO-0122362 A1 | 3/2001 |
| WO | WO-0185030 A1 | 11/2001 |
| WO | WO-0229758 A2 | 4/2002 |
| WO | WO-0229764 A1 | 4/2002 |
| WO | WO-02095686 A1 | 11/2002 |
| WO | WO-03034336 A2 | 4/2003 |
| WO | WO-03060553 A2 | 7/2003 |
| WO | WO-03081529 A1 | 10/2003 |
| WO | WO-2004010374 A2 | 1/2004 |
| WO | WO-2004012152 A2 | 2/2004 |
| WO | WO-2004066807 A2 | 8/2004 |
| WO | WO-2004068406 A2 | 8/2004 |
| WO | WO-2004072903 A2 | 8/2004 |
| WO | WO-2005004038 A1 | 1/2005 |
| WO | WO-2005004721 A1 | 1/2005 |
| WO | WO-2005027765 A1 | 3/2005 |
| WO | WO-2005031635 A1 | 4/2005 |
| WO | WO-2005083633 A2 | 9/2005 |
| WO | WO-2005119578 A2 | 12/2005 |
| WO | WO-2006002353 A2 | 1/2006 |
| WO | WO-2006020920 A2 | 2/2006 |
| WO | WO-2006061815 A1 | 6/2006 |
| WO | WO-2006066122 A2 | 6/2006 |
| WO | WO-2006079042 A2 | 7/2006 |
| WO | WO-2006082558 A2 | 8/2006 |
| WO | WO-2007020555 A2 | 2/2007 |
| WO | WO-2007066249 A2 | 6/2007 |
| WO | WO-2007102858 A1 | 9/2007 |
| WO | WO-2007146930 A2 | 12/2007 |
| WO | WO-2008030192 A1 | 3/2008 |
| WO | WO-2009007910 A2 | 1/2009 |
| WO | WO-2009056147 A1 | 5/2009 |
| WO | WO-2010020933 A2 | 2/2010 |
| WO | WO-2010033971 A1 | 3/2010 |
| WO | WO-2010061335 A1 | 6/2010 |
| WO | WO-2010086810 A1 | 8/2010 |
| WO | WO-2011015822 A1 | 2/2011 |
| WO | WO-2011038044 A2 | 3/2011 |
| WO | WO-2012021307 A2 | 2/2012 |

OTHER PUBLICATIONS

Coupling between lumped and distributed models for blood flow problems, Quarteroni et al., Comput Visual Sci 4: 111-124, 2001.
Experimental and Computational Flow Evaluation of Coronary Stents, Berry et al., Annals of Biomedical Engineering, 28: 386-398, 2000.
Factors Influencing Blood Flow Patterns in the Human Right Coronary Artery, Myers et al., Annals of Biomedical Engineering, 29:109-120, 2001.
Multiscale modeling of the cardiovascular system: application to the study of pulmonary and coronary perfusions in the univentricular circulation, Lagana et al., Journal of Biomechanics 38: 1129-1141, 2005.
Numerical Simulation of Pulsatile Flow in a Compliant Curved Tube Model of a Coronary Artery, Qiu et al., Journal of Biomedichanical Engineering 122:77-85, 2000.
Numerical Treatment of Defective Boundary Conditions for the Navier-Stokes Equations, Formaggia et al., Siam J. Numer, Anal. 40(1),:376-401, 2002.
Strain distribution over plaques in human coronary arteries relates to shear stress, Gijsen et al., Am J. Physioi Heart Circ Physiol 295: H1608-H1614, 2008.
Validated computation of physiologic flow in a realistic coronary artery branch, Perktold et al., Journal of Biomechanics 31:217-228, 1998.
Zhang et al., "Perspective on CFD studies of coronary artery disease lesions and hemodynamics: A review"; International Journal for Numerical Methods in Biomedical Engineering, (2014); pp. 1-22.
Jung E., et al., "Lumped Parameter Models of Cardiovascular Circulation in Normal and Arrhythmia Cases," Journal of the Korean Mathematical Society, 2006, vol. 43, pp. 885-897.
Koo B.K., et al., "Diagnosis of Ischemia-Causing Coronary Stenoses by Noninvasive Fractional Flow Reserve Computed from Coronary Computed Tomographic Angiograms. Results from the Prospective Multicenter Discover-Flow(Diagnosis of Ischemia-Causing Stenoses Obtained Via Noninvasive Fractional Flow Reserve) study," Journal of the American College of Cardiology, 2011, vol. 58 (19), pp. 1989-1997.
Shim E.B., et al., "Mathematical Modeling of Cardiovascular System Dynamics Using a Lumped Parameter Method," The Japanese Journal of Physiology, 2004, vol. 54 (6), pp. 545-553.
Yang G.Z., et al., "Flow and Myocardial Interaction: an Imaging Perspective," Philosophical Transactions of the Royal Society of London. Series B, Biological Sciences, Aug. 29, 2007, vol. 362 (1484), pp. 1329-1341.
Al-Saadi N., et al., "Noninvasive Detection of Myocardial Ischemia from Perfusion Reserve Based on Cardiovascular Magnetic Resonance," Circulation, 2000, vol. 101 (12), pp. 1379-1383.
Anderson H.V., et al., "Coronary Artery Flow Velocity is Related to Lumen Area and Regional Left Ventricular Mass," Circulation, 2000, vol. 102 (1), pp. 48-54.
Antiga L., et al., "An Image-Based Modeling Framework for Patient-Specific Computational Hemodynamics," Medical & Biological Engineering & Computing, Nov. 2008, vol. 46 (11), pp. 1097-1112.
Arkilic E.B., et al., "Mass Flow and Tangential Momentum Accommodation in Silicon Micromachined Channels," Journal of Fluid Mechanics, 2001, vol. 437, pp. 29-43.
Bekkers E. J., et al., "Multiscale Vascular Surface Model Generation from Medical Imaging Data Using Hierarchical Features," IEEE Transactions on Medical Imaging, 2008, vol. 27 (3), pp. 331-341.
Benson L.N., et al., "Percutaneous Implantation of a Balloon-Expandable Endoprosthesis for Pulmonary Artery Stenosis: An Experimental Study," Journal of the American College of Cardiology, 1991, vol. 18 (5), pp. 1303-1308.
Bernhard S., et al., "Transient Integral Boundary Layer Method to Calculate the Translesional Pressure Drop and the Fractional Flow Reserve in Myocardial Bridges," BioMedical Engineering OnLine, 2006, vol. 5, p. 42.
Bishop A.H., et al., "Fractional Flow Reserve Critical Review of an Important Physiological Adjunct to Angiography," American Heart Journal, 2004, vol. 147 (5), pp. 792-802.
Botman K.J., et al., "Percutaneous Coronary Intervention or ByPass Surgery in Multivessel Disease: A tailored approach based on Coronary Pressure Measurement," Catheterization and Cardiovascular Interventions, 2004, vol. 63 (2), pp. 184-191.
Bottcher M., et al., "Effect of Oral Nitroglycerin and Cold Stress on Myocardial Perfusion in Areas Subtended by Stenosed and Nonstenosed Coronary Arteries," American Journal of Cardiology, 2002, vol. 89 (9), pp. 1019-1024.
Byorigaku-Rinsho, Rubin Igaku heno Kiban- translated as Pathology-Foundation for Clinical Medicine (published on Nov. 6, 2007), Emanuel Rubin Ed, Toshimitsu Suzuki, Hideo Nakamura, Masahisa Fukayama, Mitsutoku Yamakawa, Tadashi Yoshino(translation supervisor), Nishimura Co, Ltd, pp. 426-432.
Chambers J., et al., "The Peak to Mean Pressure Decrease Ratio: A New Method of Assessing Aortic Stenosis," Journal of the American Society of Echocardiography, 2005, vol. 18 (6), pp. 674-678.
Chen S., et al., "Lattice Boltzmann Method for Fluid Flows," Annual Review of Fluid Mechanics, 1998, vol. 30, pp. 329-364.

(56) References Cited

OTHER PUBLICATIONS

Choy J.S., et al., "Scaling of Myocardial Mass to Flow and Morphometry of Coronary Arterie," Journal of Applied Physiology, 2008, vol. 104 (5), pp. 1281-1286.
Cilla M., et al., "Machine Learning Techniques as a Helpful Tool Toward Determination of Plaque Vulnerability," IEEE Transactions on Biomedical Engineering, 2012, vol. 59 (4), pp. 1155-1161.
De Bruyne B., et al., "Simultaneous Coronary Pressure and Flow Velocity Measurements in Humans. Feasibility, Reproducibility, and Hemodynamic Dependence of Coronary Flow Velocity Reserve, Hyperemic Flow Versus Pressure Slope Index, and Fractional Flow Reserve," Circulation, 1996, vol. 94 (8), pp. 1842-1849.
Deschamps T., et al., "Vessel Segmentation and Blood Flow Simulation Using Level-Sets and Embedded Boundary Methods," International Congress Series, 2004, vol. 1268, pp. 75-80.
Ellwein L.M., et al., "Sensitivity Analysis and Model Assessment: Mathematical Models for Arterial Blood Flow and Blood Pressure," Cardiovascular Engineering, 2008, vol. 8 (2), pp. 94-108.
Erglis A., et al., "Non-invasive FFR Using Coronary CT Angiography and Computational Fluid Dynamics Predicts the Hemodynamic Significance of Coronary Lesions," 2010, 19 pages.
European Search Report for Application No. EP14189381, dated Feb. 16, 2015, 8 pages.
European Search Report for Application No. EP15178021, dated Oct. 30, 2015, 8 pages.
European Search Report for Application No. EP17155303, dated May 24, 2017, 7 pages.
Figueroa C.A., et al., "A Coupled-momentum Method to Model Blood Flow and Vessel Deformation in Human Arteries: Applications in Disease Research and Simulation-Based Medical Planning," 2006, pp. 214.
Final Office Action dated May 1, 2012 for U.S. Appl. No. 13/290,842, filed Nov. 7, 2011.
Final Office Action dated Jul. 3, 2012 for U.S. Appl. No. 13/290,641, filed Nov. 7, 2011.
Final Office Action dated Jun. 29, 2012 for U.S. Appl. No. 13/013,561 filed Jan. 25, 2011.
Fischer A.M., et al., "Predicting Plaque Rupture: Enhancing Diagnosis and Clinical Decision-Making in Coronary Artery Disease," Vascular Medicine, 2000, vol. 5 (3), pp. 163-172.
Forster S., et al., "Tc-99m Sestamibi Single Photon Emission Computed Tomography for Guiding Percutaneous Coronary Intervention in Patients with Multivessel Disease: A Comparison with Quantitative Coronary Angiography and Fractional Flow Reserve," the International Journal of Cardiovascular Imaging, 2010, vol. 26 (2), pp. 203-213.
Frauenfelder T., et al., "In-vivo Flow Simulation in Coronary Arteries Based on Computed Tomography Data Sets: Feasibility and Initial Results," European Radiology, 2007, vol. 17 (5), pp. 1291-1300.
Hamada M., et al., "Shinkakudai no Hasseikijyo (Mechanism of Development of Heart Enlargement)," Modern Physician, Shinkoh-IgakuShuppan Co. Ltd, 1997, vol. 17 (8), pp. 967-970.
Himeno R., et al., "Blood Flow Simulation and its application to Medical Treatment," Journal of the Japan Society of Precision Engineering, 2005, vol. 71 (4), pp. 427-430.
Kassab G.S., et al., "Morphometry of Pig Coronary Arterial Trees," American Journal of Physiology, 1993, vol. 265, pp. H350-H365.
Kim H.J., et al., "On Coupling a Lumped Parameter Heart Model and a Three-Dimensional Finite Element Aorta Model," Annals of Biomedical Engineering, 2009, vol. 37 (11), pp. 2153-2169.
Kim H.J., et al., "Patient-Specific Modeling of Blood Flow and Pressure in Human Coronary Arteries," Annals of Biomedical Engineering, 2010, vol. 38 (10), pp. 3195-3209.
Kock S.A., et al., "Mechanical Stresses in Carotid Plaques using MRI-Based Fluid-Structure Interaction Models," Journal of Biomechanics, 2008, vol. 41 (8), pp. 1651-1658.
Kristensen T.S., et al., "Correlation Between Coronary Computed Tomographic Angiography and Fractional Flow Reserve," International Journal of Cardiology, 2010, vol. 144 (2), pp. 200-205.

Ku J.P., et al., "In Vivo Validation of Numerical Prediction of Blood Flow in Arterial Bypass Grafts," Annals of Biomedical Engineering, 2002, vol. 30 (6), pp. 743-752.
Kurita T., et al., "Regional Myocardial Perfusion Reserve Determined Using Myocardial Perfusion Magnetic Resonance Imaging Showed a Direct Correlation With Coronary Flow Velocity Reserve by Doppler Flow Wire," European Heart Journal, 2009, vol. 30 (4), pp. 444-452.
Latifoglu F., et al., "Medical Diagnosis of Atherosclerosis from Carotid Artery Doppler Signals using Principal Component Analysis (PCA), k-NN based weighting pre-processing and Artificial Immune Recognition system (AIRS)," Journal of Biomedical Informatics, 2008, vol. 41 (1), pp. 15-23.
Le H., et al., "Estimation of Regional Myocardial Mass at Risk Based on Distal Arterial Lumen Volume and Length Using 3d Micro-Ct Images," Computerized Medical Imaging and Graphics, 2008, vol. 32 (6), pp. 488-501.
Lee D.C., et al., "Quantification of Absolute Myocardial Blood Flow by Magnetic Resonance Perfusion Imaging," JACC Cardiovascular Imaging, 2009, vol. 2 (6), pp. 761-770.
Lee K.W., et al., "Ultrasound Image-Based Computer Model of a Common Carotid Artery with a Plaque," Medical Engineering and Physics, 2004, vol. 26 (10), pp. 823-840.
Lesage D., et al., "A Review of 3d Vessel Lumen Segmentation Techniques: Models, Features and Extraction Schemes," Medical Image Analysis, 2009, vol. 13 (6), pp. 819-845.
Leuprecht A., et al., "Blood Flow in the Human Ascending Aorta: a Combined MRI and CFD Study," Journal of Engineering Mathematics, 2003, vol. 47 (3), pp. 387-404.
Lim C.Y., et al., "Application of lattice Boltzmann method to simulate microchannel flows," Physics of Fluids, 2002, vol. 14 (7), pp. 2299-2308.
Liu D., et al., "Computational Analysis of Oxygen Transport in the Retinal Arterial Network," Current Eye Research, 2009, vol. 34 (11), pp. 945-956.
Liu H., et al., "Multi-scale Simulation of Circulatory System," Journal of the Japan Society of Precision Engineering, 2005, vol. 71 (12), pp. 1492-1497.
Malek A.M., et al., "Hemodynamic Shear Stress and Its Role in Atherosclerosis," JAMA, 1999, vol. 282 (21), pp. 2035-2042.
Marshall W.W., et al., "Use of a Secure Internet Web Site for Collaborative Medical Research," JAMA, 2000, vol. 284 (14), pp. 1843-1849.
Melikian N., et al., "Fractional Flow Reserve and Myocardial Perfusion Imaging in Patients with Angiographic Multivessel Coronary Artery Disea," JACC: Cardiovascular Interventions, 2010, vol. 3 (3), pp. 307-314.
Morris P.D., et al., "Virtual Fractional Flow Reserve from Coronary Angiography: Modeling the Significance of Coronary Lesions: Results From the VIRTU-1 (VIRTUal Fractional Flow Reserve From Coronary Angiography) Study," JACC: Cardiovascular Interventions, 2013, vol. 6 (2), pp. 149-157.
Motoyama S., et al., "Computed Tomographic Angiography Characteristics of Atherosclerotic Plaques Subsequently Resulting in Acute Coronary Syndrome," Journal of the American College of Cardiology, 2009, vol. 54 (1), pp. 49-57.
Nagai H., et al., "Advance in Imaging-Technology for Cardiac Area Analysis," The Institute of Electronics Information and Communication Engineers Technical Report, Iryogazo, 2007, vol. 106 (510), pp. 147-149.
Nagel E., et al., "Magnetic Resonance Perfusion Measurements for the Noninvasive Detection of Coronary Artery Disease," Circulation, 2003, vol. 108 (4), pp. 432-437.
Neal M.L., et al., "Current Progress in Patient-Specific Modeling," Briefings in Bioinformatics, 2010, vol. 11 (1), pp. 111-126.
Non-Final Office Action dated Feb. 3, 2012 for U.S. Appl. No. 13/290,476, filed Nov. 7, 2011.
Non-Final Office Action dated Apr. 4, 2012 for U.S. Appl. No. 12/661,491, filed Mar. 17, 2010.
Non-Final Office Action dated Apr. 8, 2013 for U.S. Appl. No. 13/014,809, filed Jan. 27, 2011.
Non-Final Office Action dated Apr. 11, 2012 for U.S. Appl. No. 13/014,835, filed Jan. 27, 2011.

(56) References Cited

OTHER PUBLICATIONS

Non-Final Office Action dated May 11, 2012 for U.S. Appl. No. 13/291,089 filed, Nov. 7, 2011.
Non-Final Office Action dated Apr. 12, 2012 for U.S. Appl. No. 13/014,857, filed Jan. 27, 2011.
Non-Final Office Action dated Mar. 13, 2012 for U.S. Appl. No. 13/290,641, filed Nov. 7, 2011.
Non-Final Office Action dated Apr. 16, 2012 for U.S. Appl. No. 13/014,841, filed Jan. 27, 2011.
Non-Final Office Action dated Apr. 18, 2012 for U.S. Appl. No. 13/014,845, filed Jan. 27, 2011.
Non-Final Office Action dated Apr. 19, 2012 for U.S. Appl. No. 13/014,850, filed Jan. 27, 2011.
Non-Final Office Action dated Apr. 22, 2013 for U.S. Appl. No. 13/014,821, filed Jan. 27, 2011.
Non-Final Office Action dated Jun. 22, 2012 for U.S. Appl. No. 13/014,829, filed Jan. 27, 2011.
Non-Final Office Action dated Feb. 23, 2012 for U.S. Appl. No. 13/013,561, filed Jan. 25, 2011.
Non-Final Office Action dated May 25, 2012 for U.S. Appl. No. 13/291,077, filed Nov. 7, 2011.
Non-Final Office Action dated Jan. 26, 2012 for U.S. Appl. No. 13/290,842, filed Nov. 7, 2011.
Ohashi T., et al., "Computational Analysis of the Stress and Strains with in an Atherosclerotic Plaque Exerted by Interaction Between the Blood Flow and the Vessel Wall Structure, Proceedings of the JSME Bioengineering Conference and Seminar," The Japan Society of Mechanical Engineers, 2000, vol. 11, pp. 103-104.
Olufsen M.S., et al., "Modeling Heart Rate Regulation—Part I: Sit-to-Stand Versus Head-Up Tilt," Cardiovascular Engineering—an International Journal, 2008, vol. 8 (2), pp. 73-87.
Olufsen M.S., et al., "On Deriving Lumped Models for Blood Flow and Pressure in the Systemic Arteries," Mathematical Biosciences and Engineering, 2004, vol. 1 (1), pp. 61-80, Retrieved from the Internet: URL:http://www4.ncsu.edu/~msolufse/OlufsenNadim.pdf,[retrieved on Jul. 15, 2015], XP055202425.
Partial European Search Report for Application No. EP14189383, dated May 26, 2015, 8 pages.
Pekkan K., et al., "Patient-Specific Surgical Planning and Hemodynamic Computational Fluid Dynamics Optimization Through Free-Form Haptic Anatomy Editing Tool (SURGEM), " Medical and Biological Engineering and Computing, 2008, vol. 46 (11), pp. 1139-1152.
Pereztol V., et al., "Correspondence Between Left Ventricular 17 Myocardial Segments and Coronary Arteries," European Heart Journal, 2005, vol. 26 (24), pp. 2637-2643.
Pijls N.H., et al., "Measurement of Fractional Flow Reserve to Assess the Functional Severity of Coronary-Artery Stenoses," New England Journal of Medicine, 1996, vol. 334 (26), pp. 1703- 1708.
Pijls N.H., et al., "Percutaneous Coronary Intervention of Functionally Nonsignificant Stenosis: 5-year follow-up of the DEFER Study," Journal of the American College of Cardiology, 2007, vol. 49 (21), pp. 2105-2111.
Pinciroli F., et al., "ARCADIA: A System for the Integration of Angiocardiographic Data and Images by an Object-Oriented DBMS," Computers and Biomedical Research, 1995, vol. 28 (1), pp. 5-23.
Qian Y., et al., "Computational Hemodynamic Analysis in Congenital Heart Disease: Simulation of the Norwood Procedure, "Annals of Biomedical Engineering, 2010, vol. 38 (7), pp. 2302-2313.
Quarteroni A., et al., "On the Mathematical Modeling of the Cardiovascular System (Invited Lectures in the 12.sup.th JSIAM Annual Meeting), Bulletin," The Japan Society for Industrial and Applied Mathematics, 2003, vol. 13 (1), pp. 79-82.
Rieber J., et al., "Cardiac Magnetic Resonance Perfusion Imaging for the Functional Assessment of Coronary Artery Disease: A Comparison with Coronary Angiography and Fractional Flow Reserve, " European Heart Journal, 2006, vol. 27 (12), pp. 1465-1471.
Rong T.U., et al., "3D Reconstruction of Coronary Arteries from Two X-ray Angiograms based on Anatomic Model," Proceeding of the International Society for Optics and Photonics, 2007, vol. 6534, 8 page.
Sakamoto A., et al., Hyojun Byorigaku [translated as Standard Pathology] 4th Ed (published on Aug. 1, 2010), Atsuhiko Sakamoto, Masanobu Kitagawa, Toshiro Niki (Ed.), Igaku Shoin Ltd, pp. 324-330.
Sakamoto A., et al., Hyojun Byorigaku [translated as Standard Pathology] 4th Ed (published on Aug. 1, 2010), Atsuhiko Sakamoto, Masanobu Kitagawa, Toshiro Niki (Ed.), Igaku Shoin Ltd, pp. 345-349.
Schroeder T., et al., "Cerebral Hyperfusion Following Carotid Endarterectomy," Journal of Neurosurgery, 1987, vol. 66 (6), pp. 824-829.
Schwarz S., et al., "Effects of Induced Hypertension on Intracranial Pressure and Flow Velocities of the Middle Cerebral Arteries in Patients with Large Hemispheric Stroke," Stroke, 2002, vol. 33 (4), pp. 998-1004.
Shalman E., et al., "Numerical Modeling of the Flow in Stenosed Coronary Artery. The Relationship Between Main Hemodynamic Parameters," Computers in Biology and Medicine, 2002, vol. 32 (5), pp. 329-344.
Shalman E., et al., "Pressure-based Simultaneous CFR and FFR Measurements: Understanding the Physiology of a Stenosed Vessel," Computers in Biology and Medicine, 2001, vol. 31 (5), pp. 353-363.
Spilker R.L., et al., "Models and Methods in Computational Vascular and Cardiovascular Mechanics, 9th U.S. National Congress on Computational Mechanics," 2007, 1 page.
Spilker R.L., et al., "Morphometry-Based Impedance Boundary Conditions for Patient-Specific Modeling of Blood Flow in Pulmonary Arteries," Annals of Biomedical Engineering, 2007, vol. 35 (4), pp. 546-559.
Spilker R.L., et al., "Tuning Multidomain Hemodynamic Simulations to Match Physiological Measurements," Annals of Biomedical Engineering, 2010, vol. 38 (8), pp. 2635-2648.
Steele B.N., et al., "In vivo Validation of a One-Dimensional Finite-Element Method for Predicting Blood Flow in Cardiovascular Bypass Grafts," IEEE Transactins on Biomedical Engineering, 2003, vol. 50 (6), pp. 649-656.
Steinman D.A., et al., "Flow Imaging and Computing: Large Artery Hemodynamics," Annals of Biomedical Engineering, 2005, vol. 33 (12), pp. 1704-1709.
Steinman D.A., et al., "Image-Based Computational Fluid Dynamics Modeling in Realistic Arterial Geometries," Annals of Biomedical Engineering, 2002, vol. 30 (4), pp. 483-497.
Sud V.K., et al., "Simulation of Steady Cardiovascular Flow in the Presence of Stenosis using a Finite Element Method," Physics in Medicine and Biology, 1990, vol. 35 (7), pp. 947-959.
Suttorp M.J., et al., "Primary Stenting of Totally Occluded Native Coronary Arteries II (PRISON II): a Randomized Comparison of Bare Metal Stent Implantation with Sirolimus-Eluting Stent Implantation for the Treatment of Total Coronary Occlusions," Circulation, 2006, vol. 114 (9), pp. 921-928.
Tang D., et al., "Local Maximal Stress Hypothesis and Computational Plaque Vulnerability Index for Atherosclerotic Plaque Assessment," Annals of Biomedical Engineering, 2005, vol. 33 (12), pp. 1789-1801.
Taylor C.A., et al., "A Computational Framework for Investigating Hemodynamic Factors in Vascular Adaptation and Disease," 1996, 118 pages.
Taylor C.A., et al., "Computational Investigations in Vascular Disease," Computers in Physics, 1996, vol. 10 (3), pp. 224-232.
Taylor C.A., et al., "Image-Based Modeling of Blood Flow and Vessel Wall Dynamics: Applications, Methods and Future Directions: Sixth International Bio-Fluid Mechanics Symposium and Workshop, Mar. 28-30, 2008 Pasadena, California.," Annals of Biomedical Engineering, 2010, vol. 38 (3), pp. 1188-1203.
Taylor C.A., et al., "Open Problems in Computational Vascular Biomechanics: Hemodynamics and Arterial Wall Mechanics," Computer Methods in Applied Mechanics and Engineering, 2009, vol. 198 (45-46), pp. 3514-3523.
Taylor C.A., et al., "Patient-Specific Modeling of Cardiovascular Mechanics," Annual Review of Biomedical Engineering, 2009, vol. 11, pp. 109-134.

(56) References Cited

OTHER PUBLICATIONS

Taylor C.A., et al., "Predictive Medicine: Computational Techniques in Therapeutic Decision-Making," Computer Aided Surgery, 1999, vol. 4 (5), pp. 231-247.
Taylor C.A., et al., "The HeartFlow Concept Combining Angiographic Imaging and Noninvasive Hemodynamic Lesion Assessment: Technology Description," Transcatheter Cardiovascular Therapeutics (TCT) Conference, 2010, 12 pages.
Termeer M., et al., "Visualization of Myocardial Perfusion Derived from Coronary Anatomy," IEEE Transactions on Visualization and Computer Graphics, 2008, vol. 14 (6), pp. 1595-1602.
U.S. Appl. No. 61/210,401, Inventor name: Charles A. Taylor et al., Title: Patient-Specific Hemodynamics of the Cardiovascular System, filed Mar. 17, 2009.
Vignon-Clementel I.E., et al., "Outflow Boundary Conditions for Three-Dimensional Finite Element Modeling of Blood Flow and Pressure in Arteries," Computer Methods in Applied Mechanics and Engineering, 2006, vol. 195 (29-32), pp. 3776-3796.
Wang K.C., et al., "Improving Geometric Model Construction for Blood Flow Modeling," IEEE Engineering in Medicine and Biology, 1999, vol. 18 (6), pp. 33-39.
Watkins S., et al., "Validation of Magnetic Resonance Myocardial Perfusion Imaging With Fractional Flow Reserve for the Detection of Significant Coronary Heart Disease," Circulation, 2009, vol. 120, pp. 2207-2213.
Wilson N., et al., "A Software Framework for Creating Patient Specific Geometric Models from Medical Imaging Data for Simulation Based Medical Planning of Vascular Surgery," Medical Image Computing and Computer-Assisted Intervention—MICCAI, 2001, vol. 2208, pp. 449-456.
Wilson N.M., et al., "An Integrated Software System for Preoperatively Evaluating Aorto-Femoral Reconstruction Procedures," Summer Bioengineering Conference, 2003, pp. 899-900, [retrieved on May 5, 2015]. Retrieved from the Internet:< URL: http://www.tulane.eduj-sbc2003/pdfdocs/0899.pdf>.
Wong J.T., et al., "Determination of Fractional Flow Reserve (FFR) based on Scaling Laws: a Simulation Study," Physics in Medicine and Biology, 2008, vol. 53 (14), pp. 3995-4011.
Wood N.B., et al., "Combined MR Imaging and CFD Simulation of Flow in the Human Descending Aorta," Journal of Magnetic Resonance Imaging, 2001, vol. 13 (5), pp. 699-713.
Yin W., et al., "3D Numerical Simulation of Coronary Blood Flow and Its Effect on Endothelial Cell Activation," Engineering in Medicine and Biology Society, 2009, pp. 4003-4006.
Yokoi H., et al., "Teiryoteki Kandomyaku Zoei (QCA) no Genjo to Shorai: Translated as Current state and Future of Quantitative Coronary Angiography," Journal of a Measurement Subcommittee, 2001, vol. 9 (1), pp. 14-20.
Caramia et al., "Chapter 2: Multi-Objective Optimization", 2008, Multi-Objective Management in Freight Logistics, Springer, XVI, 187, pp. 11-36.
El Fakhri G., et al., "Quantitative Dynamic Cardiac 82Rb PET Using Generalized Factor and Compartment Analyses," Journal of Nuclear Medicine, Aug. 2005, vol. 46 (8), pp. 1264-1271.
Jerosch-Herold M., et al., "Analysis of Myocardial Perfusion MRI," Journal of Magnetic Resonance Imaging, Jun. 2004, vol. 19 (6), pp. 758-770.
Larsson, H.B., et al., "Measurement of Brain Perfusion, Blood Volume, and Blood-Brain Barrier Permeability, Using Dynamic Contrast-Enhanced T(1)-Weighted MRI at 3 Tesla", Magnetic Resonance in Medicine, Nov. 2009, vol. 62 (5), pp. 1270-1281.
Sermesant M., et al., "Toward Patient-specific Myocardial Models of the Heart," Heart Failure Clinics, Jul. 2008, vol. 4 (3), pp. 289-301.
Devault K., et al., "Blood Flow in the Circle of Willis: Modeling and Calibration," Multiscale Modeling & Simulation, Jan. 2008, vol. 7 (2), pp. 888-909.
Migliavacca F., et al., "Modeling of the Norwood Circulation: Effects of Shunt Size, Vascular Resistances, and Heart Rate," American Journal of Physiology Heart and Circulatory Physiology, May 2001, vol. 280 (5), pp. H2076-H2086.
Parkes L.M., et al., "Improved Accuracy of Human Cerebral Blood Perfusion Measurements using Arterial Spin Labeling: Accounting for Capillary Water Permeability," Magnetic Resonance in Medicine, Jul. 2002, vol. 48 (1), pp. 27-41.

\* cited by examiner

IMAGE PROCESSING METHOD FOR DETERMINING PATIENT-SPECIFIC CARDIOVASCULAR INFORMATION

CROSS-REFERENCE TO RELATED APPLICATIONS

This application claims priority from U.S. Provisional Patent Application No. 61/210,401 filed Mar. 17, 2009, which is incorporated herein by reference.

STATEMENT OF GOVERNMENT SPONSORED SUPPORT

This application is a continuation of copending U.S. patent application Ser. No. 12/661,491 filed Mar. 17, 2010, which claims the benefit of priority from US Provisional Patent Application No. 61/210,401 filed Mar. 17, 2009, which is incorporated herein by reference in their entirety.

FIELD OF THE INVENTION

This invention relates to computer-implemented methods of quantifying and predicting hemodynamic aspects of the cardiovascular system to aid in the diagnosis and treatment of coronary diseases.

BACKGROUND

The number of patients with coronary artery disease continues to rise resulting in a third of global deaths and afflicting over seventeen million individuals in the United States alone. Once patients are diagnosed with coronary artery disease using medical imaging techniques including angiography, ultrasound, and computed tomography, they are treated with medications, lifestyle changes, interventional procedures, or open heart surgery depending on the severity of their disease. Flow rate and pressure in coronary arteries are measured invasively during interventional procedures or open heart surgery. However, the information obtainable from the medical imaging techniques and the invasive flow and pressure measurement techniques are limited because the resolution of the medical imaging techniques is sufficient to visualize only the larger arteries, and the flow and pressure measurement techniques are highly invasive and restricted by time and the physical condition of the patient. However, information on coronary flow rate and the pressure of the coronary vascular beds of a patient is crucial to select treatments.

Computational simulations have proven to be useful in studying blood flow in the cardiovascular system and include research on the hemodynamics of healthy and diseased blood vessels, the design and evaluation of cardiovascular medical devices, planning of cardiovascular surgeries, and the prediction of the outcomes of interventions. However, computational simulations have been rarely used to predict pulsatile velocity and pressure fields of three-dimensional coronary vascular beds, in part because the flow rate and pressure in the coronary vascular beds are highly related to the interactions between the heart and the arterial system. Unlike flow in other parts of the arterial system, coronary flow decreases when the ventricles contract, increasing the intramyocardial pressure. Coronary flow increases when the ventricles relax, thereby, decreasing the intramyocardial pressure. Therefore, to model coronary flow and pressure realistically, it is necessary to have a model of the heart and a model of the arterial system with consideration of the interactions between the two models.

Because of this complexity in modeling coronary flow and pressure, most three-dimensional computational studies have been conducted with coronary arteries only, ignoring the interactions between the heart and the arterial system and prescribing, not predicting, coronary flow. Further, these studies have not modeled realistic pressures and generally use tractionfree outlet boundary conditions. The analytic models used as boundary conditions were coupled explicitly, necessitating either sub-iterations within the same time step or a small time step size bounded by the stability of an explicit time integration scheme. To predict the flow rate and the pressure in the coronary arterial trees of a patient realistically, computational simulations should be robust and stable enough to handle complex flow characteristics, and the coupling should be efficient and versatile to different scales of computer models.

In view of the above, there remains a need in the art for new and improved techniques for more realistic computer models of coronary flow rate and pressure.

SUMMARY OF THE INVENTION

The invention provides a noninvasive patient-specific method for aiding in the analysis, diagnosis, prediction or treatment of hemodynamics of the cardiovascular system of a patient. Coronary blood flow and pressure can be predicted using a 3-D patient image-based model that is implicitly coupled with a model of at least a portion of the remaining cardiovascular system (e.g. a lumped parameter heart model, a lumped parameter systemic vascular model, a lumped parameter pulmonary vascular model, or any combination thereof). Implicit coupling between the models in this invention is defined as the simultaneous solution at each instant of time of the equations of blood flow in both the 3-D patient image-based model and the model for at least a portion of the remainder of the cardiovascular system. The 3-D patient image-based model includes at least a portion of the thoracic aorta of the patient and at least a portion of the epicardial coronary arteries of the patient. 3-D anatomical and/or physiological data for the 3-D patient-image based model is preferably obtained via non-invasive imaging techniques or systems such as, but not limited to, computed tomography or magnetic resonance imaging. The shape of one or more shape velocity profiles at the interface of the models is enforced to have a predetermined form to control recirculating flow features or retrograde flow to minimize model instabilities and resulting in patient-specific predictions of coronary flow rate and pressure. The invention, which is implemented in a computer system, allows for patient-specific predictions of coronary flow rate and pressure under different or varying physiological states (e.g. rest, exercise, pharmacologic-induced stress, or the like) and by simulating one or more hemodynamic benefits of coronary medical interventions, percutaneous coronary interventions and surgical therapies.

DETAILED DESCRIPTION

Figure 1:
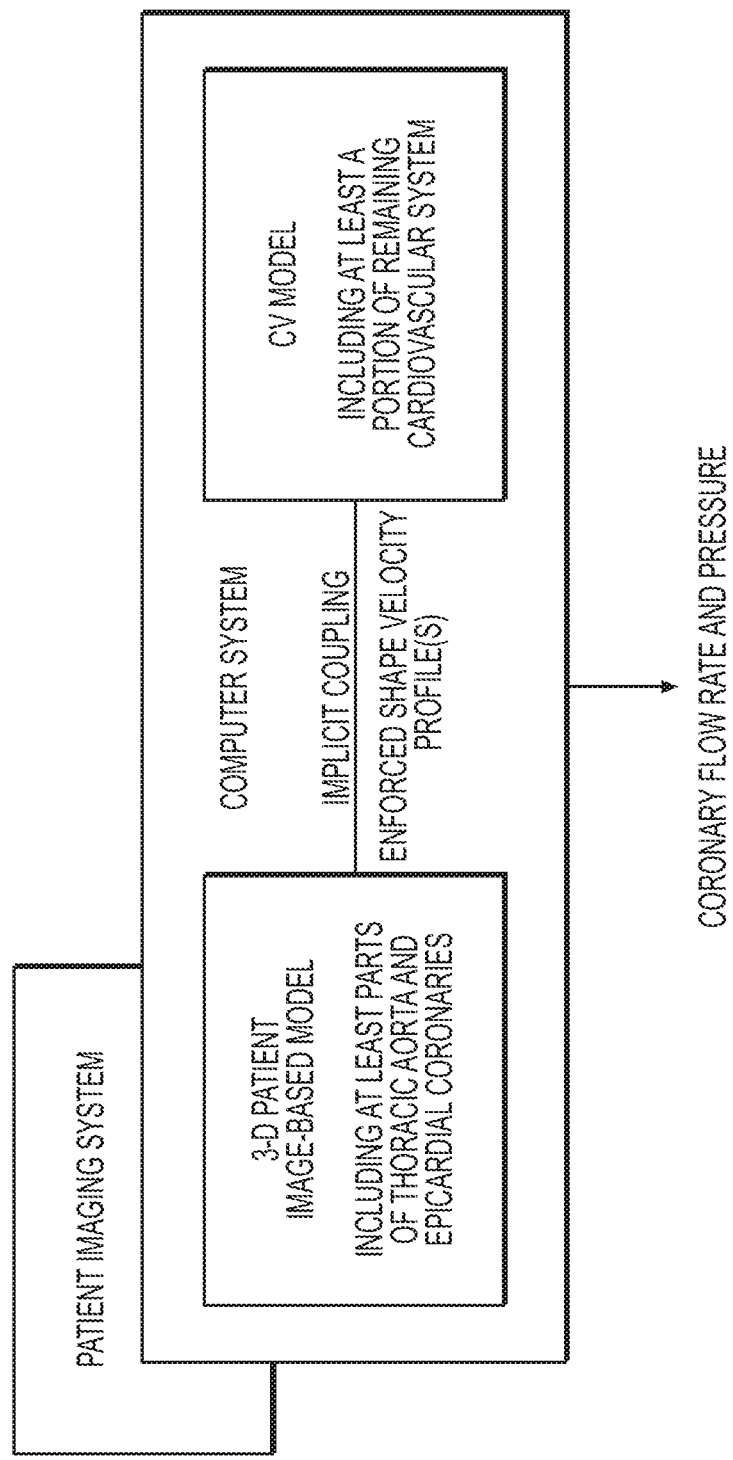
FIG. 1 shows a method and system according to an embodiment of the invention including a patient imaging system either directly or indirectly coupled to a computer system providing 3-D patient images for the 3-D patient image-based model. The 3-D patient image-based model is implicitly coupled to a model of at least a portion of the remaining cardiovascular (CV) system. The shape of at least one of the velocity profiles is enforced at the interface between the models. Coronary blood flow rate and pressure is calculated using the computer-implemented models and displayed or outputted in computer graphics or data.

Methods to calculate flow and pressure in three-dimensional coronary vascular beds are provided by considering a hybrid numerical/analytic closed loop system. For each coronary outlet of the three-dimensional finite element model, a lumped parameter coronary vascular bed model was coupled and the impedance of downstream coronary vascular networks not modeled explicitly in the computational domain was approximated. Similarly, Windkessel models were assigned to the upper branch vessels and the descending thoracic aorta to represent the rest of the arterial system. For the inlet, a lumped parameter heart model was coupled that completes a closed-loop description of the system. Using the heart model, it is possible to compute the compressive forces acting on the coronary vascular beds throughout the cardiac cycle. Further, the shape of velocity profiles of the inlet and outlet boundaries with retrograde flow was enforced to minimize numerical instabilities. The computer models solved for coronary flow and pressure as well as aortic flow and pressure in subject-specific models by considering the interactions between these model of the heart, the impedance of the systemic arterial system and the pulmonary system, and the impedance of coronary vascular beds.

Three-Dimensional Finite Element Model of Blood Flow and Vessel Wall Dynamics

Blood flow in the large vessels of the cardiovascular system can be approximated by a Newtonian fluid. Blood flow can then be solved using the incompressible Navier-Stokes equations and the motion of the vessel wall was modeled using the elastodynamics equations.

For a fluid domain $\Omega$ with boundary $\Gamma$ and solid domain $\Omega^s$ with boundary $\Gamma^s$, we solve for velocity $\vec{v}(\vec{x}, t)$, pressure $p(\vec{x}, t)$, and wall displacement $\vec{u}(\vec{x}^s, t)$ as follows:

Given $\vec{f}: \Omega \times (0, T) \to \mathbb{R}^3$, $\vec{f}^s: \Omega^s \times (0, T) \to \mathbb{R}^3$, $\vec{g}: \Gamma_g \times (0, T) \to \mathbb{R}^3$, $\vec{g}^s: \Gamma_g^s \times (0, T) \to \mathbb{R}^3$, $\vec{v}_0: \Omega \to \mathbb{R}^3$, $\vec{u}_0: \Omega^s \to \mathbb{R}^3$, and $\vec{u}_{0,t}: \Omega^s \to \mathbb{R}^3$, find $\vec{v}(\vec{x}, t)$, $p(\vec{x}, t)$, and $\vec{u}(\vec{x}^s, t)$ for $\forall \vec{x} \in \Omega$, $\forall \vec{x}^s \in \Omega^s$, and $\forall t \in (0, T)$, such that the following conditions are satisfied:

$$\rho \vec{v}_{,t} + \rho \vec{v} \cdot \nabla \vec{v} = -\nabla p + \text{div}(\tau) + \vec{f} \text{ for } (\vec{x}, t) \in \Omega \times (0, T)$$

$$\text{div}(\vec{v}) = 0 \text{ for } (\vec{x}, t) \in \Omega \times (0, T)$$

$$\rho^s \vec{u}_{,tt} = \nabla \cdot \sigma^s + \vec{f}^s \text{ for } (\vec{x}^s, t) \in \Omega^s \times (0, T)$$

where $\tau = \mu(\nabla \vec{v} + (\nabla \vec{v})^T)$ and $\sigma^s = C:\frac{1}{2}(\nabla \vec{u} + (\nabla \vec{u})^T)$ (1)

with the Dirichlet boundary conditions, $$\vec{v}(\vec{x}, t) = \vec{g}(\vec{x}, t) \text{ for } (\vec{x}, t) \in \Gamma_g \times (0, T)$$

$$\vec{u}(\vec{x}^s, t) = \vec{g}^s(\vec{x}^s, t) \text{ for } (\vec{x}^s, t) \in \Gamma_g^s \times (0, T) \quad (2)$$

the Neumann boundary conditions, $$\vec{t}_{\vec{n}} = [-pI + \tau]\vec{n} = \vec{h}(\vec{v}, p, \vec{x}, t) \text{ for } \vec{x} \in \Gamma_h \quad (3)$$

and the initial conditions, $$\vec{v}(\vec{x}, 0) = \vec{v}_0(\vec{x}) \text{ for } \vec{x} \in \Omega$$

$$\vec{u}(\vec{x}^s, 0) = \vec{u}_0(\vec{x}^s) \text{ for } \vec{x}^s \in \Omega^s$$

$$\vec{u}_{,t}(\vec{x}^s, 0) = \vec{v}_{0,t}(\vec{x}^s) \text{ for } \vec{x}^s \in \Omega^s \quad (4)$$

For fluid-solid interface conditions, the conditions implemented in the coupled momentum method were used with a fixed fluid mesh assuming small displacements of the vessel wall.

The density $\rho$ and the dynamic viscosity $\mu$ of the fluid, and the density $\rho^s$ of the vessel walls are assumed to be constant. The external body force on the fluid domain is represented by $\vec{f}$. Similarly, $\vec{f}^s$ is the external body force on the solid domain, $C$ is a fourth-order tensor of material constants, and $\sigma^s$ is the vessel wall stress tensor.

A stabilized semi-discrete finite element method was utilized to use the same order piecewise polynomial spaces for velocity and pressure variables.

Boundary Conditions

The boundary $\Gamma$ of the fluid domain is divided into a Dirichlet boundary portion $\Gamma_g$ and a Neumann boundary portion $\Gamma_h$. Further, the Neumann boundary portion $\Gamma_h$ is divided into coronary surfaces $\Gamma_{h_{cor}}$, inlet surface $\Gamma_{in}$, and the set of other outlet surfaces $\Gamma'_h$, such that $\overline{(\Gamma_{h_{cor}} \cup \Gamma_{in} \cup \Gamma'_h)} = \Gamma_h$ and $\Gamma_{h_{cor}} \cap \Gamma_{in} \cap \Gamma'_h = \phi$. Note that in this example, when the aortic valve is open, the inlet surface is included in the Neumann boundary portion $\Gamma_h$, not in the Dirichlet boundary portion $\Gamma_g$, to enable coupling with a lumped parameter heart model. Therefore, the Dirichlet boundary portion $\Gamma_g$ only includes the inlet and outlet rings of the computational domain when the aortic valve is open. These rings are fixed in time and space.

Boundary Conditions for Coronary Outlets

To represent the coronary vascular beds absent in the computational domain, a lumped parameter coronary vascular model was used (FIGS. 2-5). The coronary venous microcirculation compliance was eliminated from the original model to simplify the numerics without affecting the shape of the flow and pressure waveforms significantly. Each coronary vascular bed model includes coronary arterial resistance $R_a$, coronary arterial compliance $C_a$, coronary arterial microcirculation resistance $R_{a\text{-}micro}$, myocardial compliance $C_{im}$, coronary venous microcirculation resistance $R_{v\text{-}micro}$, coronary venous resistance $R_v$, and intramyocardial pressure $P_{im}(t)$.

For each coronary outlet $$\Gamma_{h_{cor_k}}$$

of the three-dimensional finite element model where $$\Gamma_{h_{cor_k}} \subseteq \Gamma_{h_{cor}},$$

the lumped parameter coronary vascular model was implicitly coupled using the continuity of mass and momentum operators of the coupled multidomain method as follows:

$$[M_m(\vec{v}, p) + H_m] = \tag{5}$$

$$-\left(R\int_{\Gamma_{h_{cor_k}}} \vec{v}(t)\cdot\vec{n}d\Gamma + \int_0^t e^{\lambda_1(t-s)} Z_1 \int_{\Gamma_{h_{cor_k}}} \vec{v}(s)\cdot\vec{n}d\Gamma \, ds\right) l +$$

$$\left(\int_0^t e^{\lambda_2(t-s)} Z_2 \int_{\Gamma_{h_{cor_k}}} \vec{v}(s)\cdot\vec{n}d\Gamma \, ds - \vec{n}\cdot\tau\cdot\vec{n}\right) l +$$

$$\tau - (Ae^{\lambda_1 t} + Be^{\lambda_2 t}) l -$$

$$\left(\int_0^t e^{\lambda_1(t-s)} \cdot Y_1 P_{im}(s) ds + \int_0^t e^{\lambda_2(t-s)} \cdot Y_2 P_{im}(s) ds\right) l$$

$$[M_c(\vec{v}, p) + \vec{H}_c] = \vec{v}$$

where the parameters $R$, $Z_1$, $Z_2$, $A$, $B$, $Y_1$, $Y_2$, $\lambda_1$, $\lambda_2$ are derived from the lumped parameter coronary vascular models.

Figure 2:
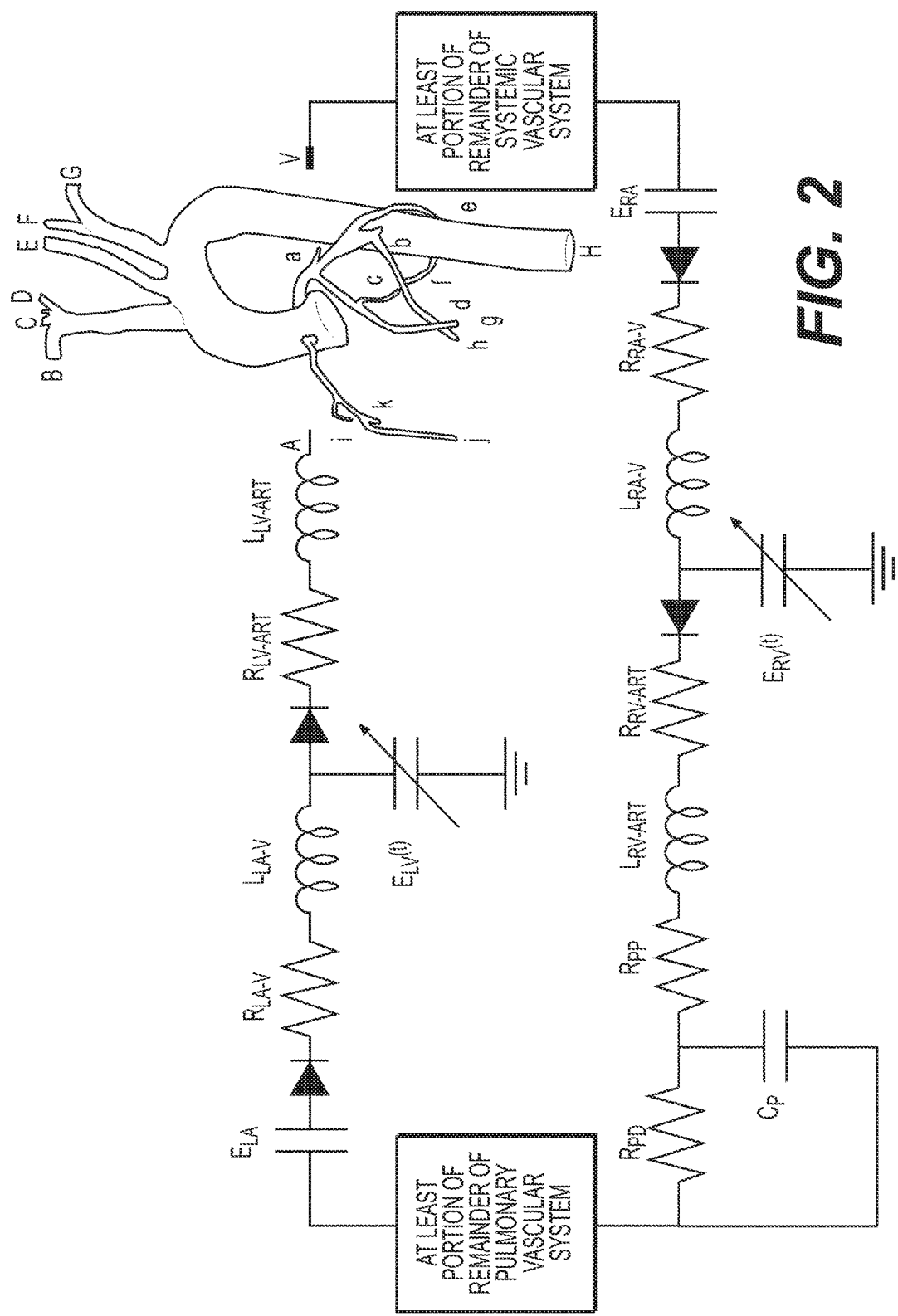
FIG. 2 is a schematic of a model of the cardiovascular system according to an embodiment of the invention including lumped parameter models of the right and left atria and ventricles. The aortic inlet is coupled to the lumped parameter model of the left ventricle at (A). All the outlets of the three-dimensional computational model feed back in the lumped model at (V). The lumped parameter models coupled to the inlet, upper branch vessels, the descending thoracic aorta, and coronary outlets for simulations of blood flow in a normal thoracic aorta model with coronary outlets under rest and exercise conditions are shown on the right. Note that all the outlets of the three-dimensional computational model feed back in the lumped model at (V).
Figure 3:
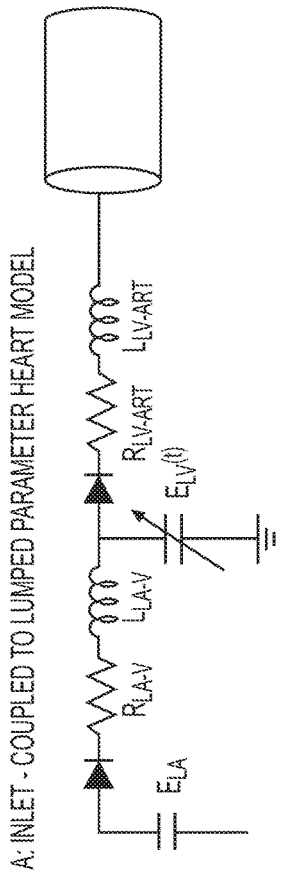
FIG. 3 shows inlet A coupled to a lumped parameter heart model according to an embodiment of the invention.
Figure 4:
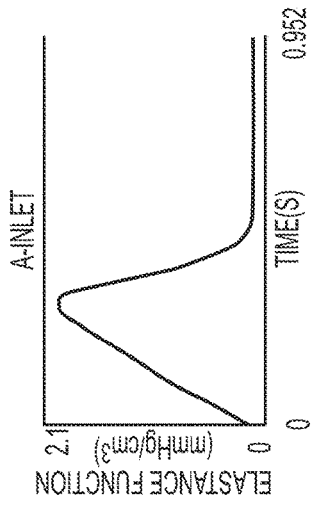
FIG. 4 shows outlets B-H coupled to three-element Windkessel models according to an embodiment of the invention.
Figure 4:
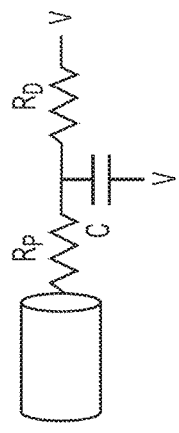
Figure 5:
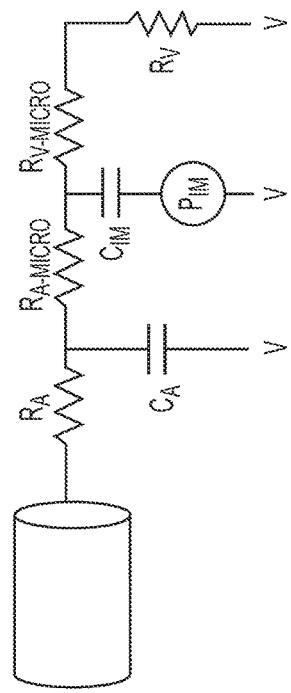
FIG. 5 shows coronary outlets a-k coupled to lumped parameter coronary vascular models according to an embodiment of the invention.

The intramyocardial pressure $P_{im}$ representing the compressive force acting on the coronary vessels due to the contraction and relaxation of the left and right ventricles was modeled with either the left or right ventricular pressure depending on the location of the coronary arteries. Both the left and right ventricular pressures were computed from two lumped parameter heart models of the closed loop system (FIGS. 2-3).

Boundary Conditions for the Inlet

The left and right sides of the heart were modeled using a lumped parameter heart model. Each heart model includes a constant atrial elastance $E_A$, atrio-ventricular valve, atrio-ventricular valvular resistance $R_{A\text{-}V}$, atrio-ventricular inductance $L_{A\text{-}V}$, ventriculo-arterial valve, ventriculo-arterial valvular resistance $R_{V\text{-}art}$, ventriculo-arterial inductance $L_{V\text{-}art}$, and time-varying ventricular elastance $E(t)$. An atrio-ventricular inductance $L_{A\text{-}V}$ and ventriculo-arterial inductance $L_{V\text{-}art}$ were added to the model to approximate the inertial effects of blood flow.

The time-varying elastance $E(t)$ models the contraction and relaxation of the left and right ventricles. Elastance is the instantaneous ratio of ventricular pressure $P_v(t)$ and ventricular volume $V_v(t)$ according to the following equation:

$$P_v(t) = E(t)\cdot[V_v(t) - V_0] \tag{6}$$

Here, $V_0$ is a constant correction volume, which is recovered when the ventricle is unloaded.

Each elastance function is derived by scaling a normalized elastance function, which remains unchanged regardless of contractility, vascular loading, heart rate and heart disease to approximate the measured cardiac output, pulse pressure and contractility of each subject.

The left side of the heart lumped parameter model is coupled to the inlet of the finite element model using a coupled multidomain method when the aortic valve is open as follows:

$$[M_m(\vec{v}, p) + H_m]_{\Gamma_{in}} = \tag{7}$$

$$-E(t)\cdot\left\{V_v(t_{ao,LV}) + \int_{t_{ao,LV}}^t \int_{\Gamma_{in}} \vec{v}\cdot\vec{n}d\Gamma \, ds - V_{LV,0}\right\} l -$$

$$\left(R_{LV\text{-}art} + L_{LV\text{-}art}\frac{d}{dt}\right)\int_{\Gamma_{in}} \vec{v}\cdot\vec{n}d\Gamma l + \tau - (\vec{n}\cdot\tau\cdot\vec{n})l$$

$$[M_c(\vec{v}, p) + \vec{H}_c]_{\Gamma_{in}} = \vec{v}\,|_{\Gamma_{in}}$$

Here, $t_{ao,LV}$ is the time the aortic valve opens. When the valve is closed, the inlet boundary is switched to a Dirichlet boundary and assigned a zero velocity condition.

Boundary Conditions for Other Outlets

For the other boundaries $\Gamma'_h$, we used the same method to couple three-element Windkessel models and modeled the continuity of momentum and mass using the following operators:

$$[M_m(\vec{v}, p) + H_m]_{\Gamma'_h} =$$

$$-\left\{R_p\int_{\Gamma'_h} \vec{v}\cdot\vec{n}\,ds + (R_p + R_d)\int_0^t \frac{e^{-(t-t_1)/\tau}}{C}\int_{\Gamma'_h} \vec{n}\,ds\,dt_1\right\} l +$$

$$\left\{\left(P(0) - R\int_{\Gamma'_h} \vec{v}(0)\cdot\vec{n}\,ds - P_d(0)\right)e^{-t/\tau} - P_d(t)\right\} l + \tau - \vec{n}\cdot\tau\cdot\vec{n}\,l$$

$$[M_c(\vec{v}, p) + \vec{H}_c]_{\Gamma'_k} = \vec{v}$$

Closed Loop Model

The boundary conditions combined with the three-dimensional finite element model of the aorta may include a closed loop model of the cardiovascular system. In most cases, the closed loop model has two lumped parameter heart models representing the left and right sides of the heart, a three-dimensional finite element model of the aorta with coronary arteries, three-element Windkessel models and lumped parameter coronary vascular models that represent the rest of the systemic circulation, and a lumped parameter model to approximate the pulmonary circulation. This closed loop model can be used to compute the right ventricular pressure, which is used to approximate the intramyocardial pressure acting on the right coronary arteries.

Parameter Values

Choice of the Parameter Values for Coronary Boundary Conditions

The boundary condition parameters determining the mean flow to each primary branch of the coronary arteries can be determined using morphology data and data from the literature. In one example, the mean coronary flow was assumed to be 4.0% of the cardiac output. For each coronary outlet surface, coronary venous resistance was calculated on the basis of the mean flow and assigned venous pressure according to literature data. The coronary arterial resistance and coronary arterial microcirculation resistance was obtained on the basis of mean flow, mean arterial pressure, and the coronary impedance spectrum using literature data. The capacitance values were adjusted to give physiologically realistic coronary flow and pressure waveforms.

In an example during simulated exercise, the mean flow to the coronary vascular bed was increased to maintain the mean flow at 4.0% of the cardiac output. The coronary parameter values for each coronary outlet surface were modified by increasing the capacitances, and the ratio of the coronary arterial resistance to the total coronary resistance.

Choice of the Parameter Values for the Inflow Boundary Condition

The parameter values of the lumped parameter heart model according to one example were determined as follows:

$$t_{max,LV} = t_{max,RV} = \begin{cases} \dfrac{T}{3}, \\ 0.5T, \end{cases}$$

at rest, where T is the measured cardiac cycle.
during exercise.

$$E_{max,LV} = \frac{\gamma \cdot R_S}{T},$$

where $R_S$ is total resistance of systemic circulation and $1 \le \gamma \le 2$.

$$E_{max,RV} = \frac{\gamma \cdot R_P}{T},$$

where $R_P$ is total resistance of pulmonary circulation and $1 \le \gamma \le 2$.

$$V_{LV,0} = V_{LV,esv} - \frac{0.9 P_{sys}}{E_{max,LV}},$$

where $V_{LV,esv}$ is an end-systolic volume of left ventricle and $P_{sys}$ is an aortic systolic pressure.

Choice of the Parameter Values for Other Outlet Boundary Conditions

For the upper branch vessels and the descending thoracic aorta in one model, three-element Windkessel models were adjusted to match mean flow distribution and the measured brachial artery pulse pressure by modifying the total resistance, capacitance, and the ratio between the proximal resistance and distal resistance based on literature data.

Constraining Shape of Velocity Profiles to Stabilize Blood Flow Simulations

Using these sets of boundary conditions, in one example, the physiologic coronary flow of subject-specific computer models were simulated. When we first simulated blood flow in complex subject-specific models with high mesh resolutions, however, we encountered instabilities in the outlet boundaries caused by complex flow structures, such as retrograde flow or complex flow propagating to the outlets from the interior domain due to vessel curvature or branches.

To resolve these instabilities, the invention further provides an augmented Lagrangian method to enforce the shape of the velocity profiles of the inlet boundary and the outlet boundaries with complex flow features or retrograde flow. The constraint functions enforce a shape of the velocity profile on a part of Neumann partition $\Gamma_{h_k}$ and minimize in-plane velocity components:

$$c_{k1}(v, x, t) = \alpha_k \int_{\Gamma_{h_k}} \left( \frac{\vec{v}(\vec{x},t) \cdot \vec{n}}{\Phi_k(\vec{v}(\vec{x},t),\vec{x},t)} - 1 \right)^2 ds = 0 \quad \vec{x} \in \Gamma_{h_k} \tag{8}$$

$$c_{ki}(\vec{v},\vec{x},t) = \alpha_k \int_{\Gamma_{h_k}} \left(\vec{v}(\vec{x},t) \cdot \vec{t}_i\right)^2 ds = 0 \quad \text{for } i = 2, 3$$

Here, $\Phi_k(\vec{v}(\vec{x}, t), \vec{x}, t)$ defines the shape of the normal velocity profile, $\vec{n}$ is the unit normal vector of face $\Gamma_{h_k}$. $\vec{t}_2$ and $\vec{t}_3$ are unit in-plane vectors which are orthogonal to each other and to the unit normal vector $\vec{n}$ at face $\Gamma_{h_k}$. $\alpha_k$ is used to nondimensionalize the constraint functions.

The boxed terms below are added to the weak form of the governing equations of blood flow and wall dynamics. The weak form becomes:

Find $\vec{v} \in S$, $p \in \mathcal{P}$ and $\vec{\lambda}_1, \vec{\lambda}_2, \ldots, \vec{\lambda}_{n_c} \in (L^2(0, T))^{n_{sd}}$, $\vec{\kappa}_k \in \mathbb{R}^{n_{sd}^+}$, Penalty numbers where $k=1, \ldots, n_c$, and $\vec{\sigma}_k \in \mathbb{R}^{n_{sd}^+}$, Regularization parameters such that $|\vec{\sigma}_k| \ll 1$, $k=1, \ldots, n_c$ such that for any and $\vec{w} \in \mathcal{W}$, $q \in \mathcal{P}$ and $\delta\vec{\lambda}_1, \delta\vec{\lambda}_2, \ldots, \delta\vec{\lambda}_{n_c} \in (L^2(0, T))^{n_{sd}}$, the following is satisfied:

$$B_G\left(\vec{w}, q, \delta\vec{\lambda}_1, \ldots, \delta\vec{\lambda}_{n_c}; \vec{v}, p, \vec{\lambda}_1, \ldots, \vec{\lambda}_{n_c}\right) = \tag{9}$$

$$\int_\Omega \left\{\vec{w} \cdot \left(\rho \vec{v}_{,t} + \rho \vec{v} \cdot \nabla \vec{v} - \vec{f}\right) + \nabla \vec{w} : (-pI + \tau)\right\} d\vec{x} -$$

$$\int_\Omega \nabla_q \cdot \vec{v} d\vec{x} - \int_{\Gamma_h} \vec{w} \cdot (-pI \cdot \tau) \cdot \vec{n} ds + \int_\Gamma q\vec{v} \cdot \vec{n} ds +$$

$$\xi \int_{\Gamma_h^s} \left\{\vec{w} \cdot \rho^s \vec{v}_{,t} + \nabla \vec{w} : \sigma^s(\vec{u}) - \vec{w} \cdot \vec{f}^s\right\} ds - \xi \int_{\partial \Gamma_h^s} \vec{w} \cdot \vec{h}^s dl +$$

$$\boxed{\begin{array}{l} \sum_{i=1}^{n_{sd}} \sum_{k=1}^{n_c} \left\{\lambda_{ki} \cdot \left(\sigma_{ki} \delta\lambda_{ki} - \delta c_{ki}(\vec{w}; \vec{v}, \vec{x}, t)\right)\right\} + \\ \sum_{i=1}^{n_{sd}} \sum_{k=1}^{n_c} \delta\lambda_{ki} \cdot \left(\sigma_{ki} \lambda_{ki} - c_{ki}(\vec{v}, \vec{x}, t)\right) \end{array}} +$$

$$\boxed{\sum_{i=1}^{n_{sd}} \sum_{k=1}^{n_c} \kappa_{ki} \cdot c_{ki}(\vec{v}, \vec{x}, t) \delta c_{ki}(\vec{w}; \vec{v}, \vec{x}, t)} = 0$$

where $\delta c_{ki}(\vec{w}; \vec{v}, \vec{x}, t) = \lim_{\epsilon \to 0} \dfrac{d c_{ki}(\vec{v} + \epsilon \vec{w}, \vec{x}, t)}{d\epsilon}$ Here, $L^2(0, T)$ represents the Hilbert space of functions that are square-integrable in time $[0,T]$. Here $n_{sd}$ is the number of spatial dimensions and is assumed to be three and $n_c$ is the number of constrained surfaces. Here, in addition to the terms required to impose the augmented Lagrangian method, the regularization term $$\sum_{i=1}^{n_{sd}} \sum_{k=1}^{n_c} 2\sigma_{ki}\lambda_{ki}\delta\lambda_{ki}$$

is added to obtain a system of equations with a non-zero diagonal block for the Lagrange multiplier degrees of freedom. This method was shown not to alter the solution significantly except in the immediate vicinity of the constrained outlet boundaries and stabilize problems that previously diverged without constraints.

TABLE 1

| | Rest | Exercise | | Rest | Exercise |
|---|---|---|---|---|---|
| Parameter values of the left and right sides of the heart | | | | | |
| $R_{LA-V}$(dynes · s/cm$^5$) | 5 | 5 | $R_{RA-V}$(dynes · s/cm$^5$) | 5 | 5 |
| $L_{LA-V}$(dynes · s$^2$/cm$^5$) | 5 | 5 | $L_{RA-V}$(dynes · s$^2$/cm$^5$) | 1 | 1 |
| $R_{LV-art}$(dynes · s/cm$^5$) | 10 | 10 | $R_{RV-art}$(dynes · s/cm$^5$) | 10 | 10 |
| $L_{LV-art}$(dynes · s$^2$/cm$^5$) | 0.69 | 0.69 | $L_{RV-art}$(dynes · s$^2$/cm$^5$) | 0.55 | 0.55 |
| $E_{LV,max}$(mmHg/cc) | 2.0 | 2.0 | $E_{RV,max}$(mmHg/cc) | 0.5 | 0.5 |
| $V_{LV,0}$(cc) | 0 | 0 | $V_{RV,0}$(cc) | 0 | 0 |
| $V_{LA,0}$(cc) | −60 | −60 | $V_{RA,0}$(cc) | −60 | −60 |
| $E_{LA}$(mmHg/cc) | 270 | 350 | $E_{RA}$(mmHg/cc) | 60 | 80 |
| Other parameter values | | | | | |
| $t_{max}$(s) | 0.33 | 0.25 | Cardiac cycle (s) | 1.0 | 0.5 |
| $R_{pp}$(dynes · s/cm$^5$) | 16 | 16 | $C_p$(cm$^5$/dynes) | 0.022 | 0.022 |
| $R_{pd}$(dynes · s/cm$^5$) | 144 | 144 | | | |

Examples of parameter values of the closed loop system at rest and during exercise for the simulations of coronary flow and pressure with normal coronary anatomy. The examples are non-limiting to the invention

TABLE 2

| Parameter values of the Windkessel models | | | |
|---|---|---|---|
| | B: Right subclavian | C: Right carotid | D: Right vertebral |
| $R_p$(10$^3$dynes · s/cm$^5$) | 1.49 | 1.41 | 10.7 |
| C(10$^{-6}$cm$^5$/dynes) | 235 | 248 | 32.9 |
| $R_d$(10$^3$dynes · s/cm$^5$) | 15.1 | 14.3 | 108 |
| | E: Left carotid | F: Left vertebral | G: Left subclavian |
| $R_p$(10$^3$dynes · s/cm$^5$) | 1.75 | 7.96 | 1.80 |
| C(10$^{-6}$cm$^5$/dynes) | 201 | 44.0 | 195 |
| $R_d$(10$^3$dynes · s/cm$^5$) | 17.6 | 80.5 | 18.2 |
| | H: Aorta (Rest) | | H: Aorta (Exercise) |
| $R_p$(10$^3$dynes · s/cm$^5$) | 0.227 | | 0.180 |
| C(10$^{-6}$cm$^5$/dynes) | 1540 | | 1600 |
| $R_d$(10$^3$dynes · s/cm$^5$) | 2.29 | | 0.722 |

Examples of parameter values of the three-element Windkessel models at rest and during exercise for the simulations of coronary flow and pressure with normal coronary anatomy. Note that the parameter values of the upper branch vessels are the same for the light exercise condition. The examples are non-limiting to the invention

TABLE 3

| | $R_a$ | $R_{a\text{-}micro}$ | $R_v + R_{v\text{-}micro}$ | $C_a$ | $C_{im}$ |
|---|---|---|---|---|---|
| Parameter values of the coronary models at rest (Resistance in 10$^3$dynes · s/cm$^5$ and capacitance in 10$^{-6}$cm$^5$/dynes) | | | | | |
| a: LAD1 | 183 | 299 | 94 | 0.34 | 2.89 |
| b: LAD2 | 131 | 214 | 67 | 0.48 | 4.04 |
| c: LAD3 | 91 | 148 | 65 | 0.49 | 4.16 |
| d: LAD4 | 55 | 90 | 40 | 0.80 | 6.82 |
| e: LCX1 | 49 | 80 | 25 | 1.28 | 10.8 |
| f: LCX2 | 160 | 261 | 82 | 0.39 | 3.31 |
| g: LCX3 | 216 | 353 | 111 | 0.29 | 2.45 |
| h: LCX4 | 170 | 277 | 87 | 0.37 | 3.12 |
| i: RCA1 | 168 | 274 | 86 | 0.37 | 3.15 |
| j: RCA2 | 236 | 385 | 121 | 0.26 | 2.24 |
| k: RCA3 | 266 | 435 | 136 | 0.23 | 1.99 |
| Parameter values of the coronary models at exercise (Resistance in 10$^3$dynes · s/cm$^5$ and capacitance in 10$^{-6}$cm$^5$/dynes) | | | | | |
| a: LAD1 | 76 | 24 | 18 | 0.75 | 6.88 |
| b: LAD2 | 52 | 16 | 13 | 1.02 | 9.34 |
| c: LAD3 | 51 | 16 | 12 | 1.07 | 9.74 |
| d: LAD4 | 31 | 10 | 7 | 0.74 | 15.9 |
| e: LCX1 | 20 | 6.2 | 5 | 2.79 | 25.4 |
| f: LCX2 | 65 | 20 | 15 | 0.85 | 7.78 |
| g: LCX3 | 87 | 27 | 21 | 0.63 | 5.74 |
| h: LCX4 | 68 | 21 | 16 | 0.80 | 7.29 |
| i: RCA1 | 71 | 22 | 16 | 0.83 | 7.60 |
| j: RCA2 | 98 | 31 | 23 | 0.59 | 5.38 |
| k: RCA3 | 110 | 35 | 25 | 0.52 | 4.72 |

Examples of parameter values of the lumped parameter models of the coronary vascular beds for the simulations of coronary flow and pressure with normal coronary anatomy. The examples are non-limiting to the invention.

The invention claimed is:

1. A method for determining cardiovascular information for a patient, the method comprising:
    receiving, using at least one computer system, patient-specific data of at least a first portion of a coronary artery of a patient's heart;
    generating, using the at least one computer system, a patient-specific geometric model of a geometry of the first portion of the patient's coronary artery, the patient-specific geometric model being generated based on the received patient-specific data;
    generating, using the at least one computer system, a lower-order patient-specific model of blood flow through a second portion of the patient's coronary artery downstream from the first portion, the lower-order patient-specific model having fewer dimensions than the patient-specific geometric model, the lower-order patient-specific model comprising one or more fluid dynamics equations and one or more blood flow parameters associated with blood flow through the second portion of the patient's coronary artery downstream from the first portion;
    determining, using the at least one computer system, fluid dynamics equations governing blood flow through the patient-specific geometric model of the geometry of the first portion of the patient's coronary artery; and
    calculating, using the at least one computer system, a value of a characteristic of blood flow through the first portion of the patient's coronary artery by implicit closed-loop coupling and simultaneous solving of both the fluid dynamics equations governing blood flow through the patient-specific geometric model and the fluid dynamics equations governing blood flow of the lower-order patient-specific model of blood flow through the second portion.

2. The method of claim 1, wherein the patient-specific geometric model comprises a three-dimensional model.

3. The method of claim 1, wherein the lower-order patient-specific model of blood flow comprises a lumped parameter model.

4. The method of claim 1, wherein the lower-order patient-specific model of blood flow comprises a lumped parameter heart model, a lumped parameter systemic vascular model, a lumped parameter pulmonary vascular model, or any combination thereof.

5. The method of claim 1, wherein the characteristic of blood flow comprises a coronary blood flow rate and/or coronary blood pressure.

6. A system for determining cardiovascular information for a patient, the system comprising:
a data storage device storing instructions for performing a method of determining cardiovascular information for a patient; and
a processor configured to execute the instructions including:
receiving, using at least one computer system, patient-specific data of at least a first portion of a coronary artery of a patient's heart;
generating, using the at least one computer system, a patient-specific geometric model of a geometry of the first portion of the patient's coronary artery, the patient-specific geometric model being generated based on the received patient-specific data;
generating, using the at least one computer system, a lower-order patient-specific model of blood flow through a second portion of the patient's coronary artery downstream from the first portion, the lower-order patient-specific model having fewer dimensions than the patient-specific geometric model, the lower-order patient-specific model comprising one or more fluid dynamics equations and one or more blood flow parameters associated with blood flow through the second portion of the patient's coronary artery downstream from the first portion;
determining, using the at least one computer system, fluid dynamics equations governing blood flow through the patient-specific geometric model of the geometry of the first portion of the patient's coronary artery; and
calculating, using the at least one computer system, a value of a characteristic of blood flow through the first portion of the patient's coronary artery by implicit closed-loop coupling and simultaneous solving of both the fluid dynamics equations governing blood flow through the patient-specific geometric model and the fluid dynamics equations governing blood flow of the lower-order patient-specific model of blood flow through the second portion.

7. The system of claim 6, wherein the patient-specific geometric model comprises a three-dimensional model.

8. The system of claim 6, wherein the lower-order patient-specific model of blood flow comprises a lumped parameter model.

9. The system of claim 6, wherein the lower-order patient-specific model of blood flow comprises a lumped parameter heart model, a lumped parameter systemic vascular model, a lumped parameter pulmonary vascular model, or any combination thereof.

10. The system of claim 6, wherein the characteristic of blood flow comprises a coronary blood flow rate and/or coronary blood pressure.

11. A non-transitory computer readable medium for use on a computer system containing computer-executable programming instructions for performing a method of determining cardiovascular information for a patient, the method comprising:
receiving, using at least one computer system, patient-specific data of at least a first portion of a coronary artery of a patient's heart;
generating, using the at least one computer system, a patient-specific geometric model of a geometry of the first portion of the patient's coronary artery, the patient-specific geometric model being generated based on the received patient-specific data;
generating, using the at least one computer system, a lower-order patient-specific model of blood flow through a second portion of the patient's coronary artery downstream from the first portion, the lower-order patient-specific model having fewer dimensions than the patient-specific geometric model, the lower-order patient-specific model comprising one or more fluid dynamics equations and one or more blood flow parameters associated with blood flow through the second portion of the patient's coronary artery downstream from the first portion;
determining, using the at least one computer system, fluid dynamics equations governing blood flow through the patient-specific geometric model of the geometry of the first portion of the patient's coronary artery; and
calculating, using the at least one computer system, a value of a characteristic of blood flow through the first portion of the patient's coronary artery by implicit closed-loop coupling and simultaneous solving of both the fluid dynamics equations governing blood flow through the patient-specific geometric model and the fluid dynamics equations governing blood flow of the lower-order patient-specific model of blood flow through the second portion.

12. The computer readable medium of claim 11, wherein the patient-specific geometric model comprises a three-dimensional model.

13. The computer readable medium of claim 11, wherein the lower-order patient-specific model of blood flow comprises a lumped parameter model.

14. The computer readable medium of claim 11, wherein the characteristic of blood flow comprises a coronary blood flow rate and/or coronary blood pressure.

* * * * *